United States Patent [19]
Thompson et al.

[11] Patent Number: 5,431,669
[45] Date of Patent: Jul. 11, 1995

[54] SURGICAL CLIP APPLIER WITH DISTAL HOOK

[75] Inventors: Todd Thompson, San Jose; Albert K. Chin, Palo Alto, both of Calif.

[73] Assignee: Origin Medsystems, Inc., Menlo Park, Calif.

[21] Appl. No.: 92,831

[22] Filed: Jul. 16, 1993

[51] Int. Cl.⁶ .............................................. A61B 17/00
[52] U.S. Cl. .................................. 606/143; 606/139; 227/902
[58] Field of Search ................ 606/139, 142–143; 227/901

[56] References Cited

U.S. PATENT DOCUMENTS

| | | |
|---|---|---|
| 3,439,523 | 4/1969 | Wood . |
| 3,584,628 | 6/1971 | Green . |
| 4,038,987 | 8/1977 | Komiya ............................. 606/142 |
| 4,509,518 | 4/1985 | McGarry et al. . |
| 4,616,650 | 10/1986 | Green et al. . |
| 4,976,722 | 12/1990 | Failla ................................ 606/157 |
| 5,084,057 | 1/1992 | Green et al. ...................... 606/142 |
| 5,156,608 | 10/1992 | Troidl et al. ..................... 602/142 |
| 5,163,945 | 11/1992 | Oritiz et al. ...................... 606/142 |
| 5,171,247 | 12/1992 | Hughett et al. .................. 606/143 |
| 5,192,288 | 3/1993 | Thompson et al. .............. 606/143 |
| 5,242,456 | 9/1993 | Nash et al. ....................... 606/142 |

FOREIGN PATENT DOCUMENTS

0629494 10/1961 Canada ............................. 606/143

Primary Examiner—Peter A. Aschenbrenner
Assistant Examiner—Jeffrey A. Schmidt
Attorney, Agent, or Firm—Townsend and Townsend; Khourie and Crew

[57] ABSTRACT

The invention provides a surgical clip applier particularly useful in laparoscopic and other least invasive surgical procedures. The clip applier includes a shaft having a distal end and a proximal end, the shaft defining an axial direction. Means are provided in the shaft for advancing a clip to the distal end. Hook means are fixed to the distal end of the shaft, the hook means having a distal portion disposed transverse to the shaft so as to define a surface facing in a proximal direction for engaging a tissue structure. A pair of movable jaws are mounted at the distal end of the shaft and are axially slidable relative to the hook means for closing a clip on a tissue structure engaged by the hook means. The movable jaws will define a U-shaped slot open in a generally distal direction. Means are further provided for advancing the jaws to a position adjacent the distal portion of the hook means, as well as means for closing the jaws. The clip applier is particularly advantageous in providing the capability to engage a tissue structure in the hook means and reposition the tissue structure and/or hold the tissue structure in tension while a surgical clip is applied.

24 Claims, 6 Drawing Sheets

SURGICAL CLIP APPLIER WITH DISTAL HOOK

BACKGROUND OF THE INVENTION

The present invention relates generally to surgical instruments for ligating body tissue structures and particularly, ligating instruments for use in least invasive surgical procedures. More specifically, the present invention relates to surgical clip appliers having movable jaws and means for holding a tissue structure in tension while a clip is applied to the structure.

In least invasive surgical (LIS) procedures, such as endoscopy, laparoscopy, pelviscopy, thoracoscopy and arthroscopy, elongated instruments of small cross-section are introduced into a body cavity through a small incision or a specialized cannula such as a trocar sleeve. Visualization is facilitated through the use of endoscopes, laparoscopes, arthroscopes and the like which have a video lens secured to a shaft for manipulation and which are connected to a video monitor viewed by the surgeon. In this way, various surgical procedures may be performed without the need for the large incisions of conventional open surgical techniques, thereby minimizing patient trauma, decreasing recovery time and reducing the risk of infection.

During LIS procedures, it is frequently necessary to ligate tissue structures such as ducts, blood vessels and the like. Such ligation is commonly accomplished using a ligation instrument specifically designed for introduction through the small incisions or cannulas used in LIS procedures. Frequently, a surgical clip applier will be used to apply U-shaped surgical clips to a tissue structure. Surgical clip appliers designed for least invasive surgical procedures such as endoscopy and laparoscopy typically have an elongated shaft with an interior axial passage, a clip closure mechanism at the distal end of the shaft, and a handle and actuator secured to the proximal end of the shaft. Desirably, such clip appliers will be capable of storing multiple clips within the shaft which are automatically fed to the closure mechanism at the distal end. In this way, the clip applier may be positioned through an incision or cannula and used to apply multiple clips within a body cavity without the necessity of removing the device to reload clips. Examples of such surgical clip appliers are seen in U.S. Pat. No. 5,084,057, U.S. Pat. No. 5,163,945 and U.S. Pat. No. 5,192,288, the complete disclosures of which are incorporated herein by reference.

Surgical clip appliers like the aforementioned generally are designed to apply surgical clips in one of two ways. In a first type of clip applier, exemplified in U.S. Pat. No. 5,163,945 ('945) or U.S. Pat. No. 5,084,057 ('057), a pair of movable jaws are mounted at the distal end of the shaft. The jaws point in a distal direction and surgical clips are fed into the jaws with the clip legs also pointing in the distal direction. Using clip appliers of this type a tissue structure is ligated by introducing the shaft into the body cavity, positioning the tissue structure between the jaws, and closing the jaws so that the clip legs are closed tightly on the structure.

In a second type of surgical clip applier, exemplified in U.S. Pat. No. 5,192,288 ('288), a stationary anvil at the distal end of the shaft provides a forming surface against which a slidable hammer moves so as to close a clip against the forming surface. Advantageously, the forming surface of the anvil is disposed at a non-zero angle, typically 90°, relative to the axial direction, so that clips are applied with the clip legs pointing in a lateral direction. Such a configuration may be advantageous for ligating tissue structures disposed in positions which are unaccessible using distally-pointing jaws. In addition, a laterally-oriented anvil provides a hook-like element for engaging the tissue structure, whereby a proximal force may be exerted on the clip applier to hold the tissue structure in tension. This allows the tissue structure to be positioned away from surrounding organs or other tissue, eliminating the risk of clipping unwanted areas, as well as improving visualization of the tissue structure to be ligated.

While surgical clip appliers designed for lateral application of clips as described in the '288 patent are advantageous in some situations, in certain procedures a surgeon may desire to apply a clip to a duct or vessel disposed in such a position that a clip applier having distally-pointing jaws as in the '945 or '057 patents will be more effective. However, using a clip applier with distally-pointing jaws, the tissue structure to be ligated will tend to be deflected away from the surgeon as the jaws are positioned around the structure so as to seat the structure against the apex of the clip. The structure may be pushed up against nearby organs or other tissue, which may be engaged in the clip if the clip is closed. Further, the tissue structure may be pushed into a position where it is obscured from view by the laparoscope or other visualization device.

For these and other reasons, an improved surgical clip applier for LIS procedures is desired which has distally-oriented jaws for applying clips with legs pointing in a distal direction, but which also has the tissue holding and tensioning capabilities of laterally-oriented closure mechanisms. The clip applier will preferably facilitate engagement, tensioning and retention of a tissue structure in a fixed position relative to the shaft of the device, so that it remains in a fixed position as the clip is applied. In this way, once the surgeon has tensioned and positioned the tissue structure as desired, the application of the clip to the structure will not change its position, which might result in overtensioning the tissue structure or interfering with unwanted organs or other tissue. Desirably, the clip applier will be introducible through a 10 mm trocar sleeve or other cannula so as to be useful in laparoscopic surgical procedures. Preferably, the clip applier will support the tissue structure on two opposing sides of the jaws to facilitate uniform tensioning and balanced support on either side of the point of ligation. Further, the clip applier should allow the tissue structure to be engaged, tensioned and ligated using a minimal number of actuators, preferably by means of a single actuator.

SUMMARY OF THE INVENTION

The invention provides a surgical clip applier particularly useful in least invasive surgical techniques, particularly laparoscopy and endoscopy. The surgical clip applier is configured for introduction through a 10 mm cannula and has an elongated configuration to reach a wide area in a body cavity. The clip applier is particularly advantageous in that it combines the convenience of distally-pointing movable jaws with the capability for engaging and retaining a tissue structure in tension while a clip is applied. The tissue structure is retained in a fixed position relative to the shaft of the clip applier, ensuring that the tissue structure remains in a known position while the clip is applied, eliminating the risk of overtensioning or interfering with nearby organs or other tissue. Additionally, the clip applier of the invention allows clips to be applied by actuating a single lever, which both positions the jaws about the tissue structure and closes the jaws to apply the clip.

In a preferred aspect of the invention, in apparatus for applying surgical clips to the tissue structure comprises a shaft having a distal end and a proximal end, the shaft defining an axial direction. Hook means are fixed to the distal end of the shaft, the hook means having a distal portion disposed transverse to the shaft so as to define a surface facing in a proximal direction for engaging a tissue structure. A pair of movable jaws defining a U-shaped slot open in the distal direction are disposed at the distal end of the shaft. The jaws are axially slidable relative to the hook means for closing a clip on a tissue structure engaged by the hook means. Means are further provided for advancing a clip along the shaft to the distal end. In addition, actuation means are provided for advancing the jaws to a position adjacent the distal portion of the hook means, as well as for closing the jaws.

In a preferred embodiment, the hook means comprises a pair of hooks extending distally from the distal end of the shaft generally parallel to the axial direction, the jaws being disposed between the hooks. In an exemplary embodiment, the hooks will have a proximal end fixed to the shaft and a distal end which is laterally deflectable. The distal ends are biased inward toward one another such that inner side faces of the hooks contact opposing lateral sides of the jaws as the jaws move distally. The pair of parallel hooks thereby supports the tissue structure on both sides of the jaws so as to facilitate application of balanced and uniform tensioning force to the tissue structure.

In a further preferred embodiment, the shaft has an axial passage from the proximal end to the distal end, and the means for advancing the jaws comprises an actuator shaft slidably disposed in the axial passage, the actuator shaft having a distal end for engaging the jaws to advance the jaws distally. In one embodiment, the jaws are fixed to a bifurcated member having a shank portion and a pair of prongs with tapered sides extending distally from the shank. The jaws will be fixed to a distal end of the prongs. The actuator shaft has an axial channel configured to slidably engage the tapered sides of the bifurcated member so as to close the jaws as the actuator shaft is advanced distally relative to the jaws. The apparatus further includes means for limiting the distal movement of the jaws to a closing position adjacent the distal portion of the hook means. In this way, the jaws will remain open as they are moved distally by the actuator shaft to the closing position, whereupon the jaws will close as the actuator shaft advances distally relative to the jaws, sliding over tapered sides of the bifurcated member.

Preferably, a handle will be secured to the proximal end of the shaft, and a lever pivotally coupled to the handle will serve to actuate the jaws. The actuator shaft is coupled to the lever, whereby pivoting the lever to a first position advances the jaws distally, and pivoting the lever from the first position to a second position closes the jaws.

In a particular embodiment, the shaft, jaws and hook means are configured to be introduced through a 10 mm trocar sleeve or other cannula. In a further preferred embodiment, a plurality of clips are retained in the shaft of the apparatus. The means for advancing the clips to distal end of the shaft may comprise a variety of mechanisms, including a belt, open channel with follower, or other means.

The invention further provides a method of applying surgical clips to a tissue structure comprising the steps of engaging tissue structure in a hook fixed to a distal end of the shaft of the clip applier; exerting a proximally-directed force on a shaft so as to hold the tissue structure in tension; advancing a U-shaped clip into a pair of movable jaws at the distal end of the shaft; distally advancing the jaws relative to the hook such that the tissue structure is disposed between the jaws; and closing the clip on the tissue structure with the legs of the clip pointing distally while holding the tissue structure in tension.

In a preferred aspect of the method, the proximally-directed force will be exerted using a handle fixed to a proximal end of a shaft, the hook being in a fixed position relative to the handle. The step of distally advancing the jaws may comprise actuating a lever coupled to the handle. Preferably, actuating the lever will further close the jaws on the tissue structure. In an exemplary embodiment, the step of advancing a clip is performed before the step of distally advancing the jaws. Alternatively, the step of advancing the clip may be performed after the step of distally advancing the jaws.

The method may further comprise the step of inserting a distal portion of the shaft through a percutaneous cannula into a body cavity, the tissue structure being disposed in the body cavity. In an exemplary embodiment the percutaneous cannula has an interior diameter of at most about 10 mm.

A further understanding of the nature and advantages of the invention will become apparent by reference to the remaining portions of the specification and drawings.

DESCRIPTION OF SPECIFIC EMBODIMENTS

The surgical clip applier of the invention generally comprises an elongated rigid shaft having distal and proximal ends and an axial passage therebetween. The shaft may be any of a variety of rigid biocompatible materials, such as stainless steel or a plastic such as acrylonitrile-butadiene-styrene (ABS), Delrin ®, polycarbonate or the like. A pair of movable jaws are mounted at the distal end of the shaft. The movable jaws define a generally U-shaped slot which is open in a generally distal direction. U-shaped (or V-shaped)

surgical clips are positioned in the jaws with the clip legs pointing distally and closed by pivoting the jaws toward one another. The surgical clips are typically stainless steel or other biocompatible alloy, and may have a variety of configurations, as described in U.S. Pat. No. 3,363,628, U.S. Pat. No. 4,976,722, U.S. Pat. No. 3,439,523, U.S. Pat. No. 4,616,650 or U.S. Pat. No. 4,509,518, the complete disclosures of which are incorporated herein by reference.

Hook means are mounted to the distal end of the shaft, the hook means providing a surface facing in a generally proximal direction against which a tissue structure may be positioned and tensioned by drawing the shaft in the proximal direction. The angle between the proximal-facing surface and the axial direction defined by the shaft proximal to the hook means may be between about 45° and 100°, but will usually be between 60° and 90°, preferably between 80° and 90°. The proximal-facing surface may also be concave with either curved or straight angular portions, so as to receive and retain a tissue structure more effectively. The hook means may take a variety of forms, including a transverse slot across a distal portion on the shaft, a transverse post or extension mounted to the distal end of the shaft, or in a preferred embodiment, a curved, hook-shaped member extending from the distal end of the shaft. Preferably, the hook means includes two generally parallel hooks extending distally from the distal end of the shaft, with the jaws disposed between the two hooks. In this way, the hook means engages and supports the tissue structure on two opposing sides of the jaws for distributed and balanced application of force to the tissue structure relative to the point of ligation. Significantly, the hook means is fixed to the shaft and unmovable relative thereto. In this way, the hook means is always disposed a fixed distance from the proximal end of the shaft so that once the user has positioned and tensioned the tissue structure in the hook means by manipulating the shaft, the tissue structure will remain in a known, fixed position as a clip is applied.

Because the hook means remains fixed relative to the shaft, the apparatus facilitates positioning a clip about a structure positioned in the hook means by distally advancing the jaws relative to the hook means until a clip held in the jaws surrounds the tissue structure. After the jaws have been advanced so that the clip is properly positioned about the tissue structure, the jaws are closed to apply the clip to the structure.

Various means may be provided for advancing the jaws and closing the jaws. Preferably, however, the mechanism for advancing and closing will require actuation of just a single lever or other actuator by the user. In a preferred embodiment, the means for advancing and closing the jaws comprises an actuator shaft slidably disposed in the axial passage of the shaft. A distal end of the actuator shaft engages the jaws and advances the jaws distally. In a further preferred aspect, the jaws have tapered sides, and the actuator shaft has an axial channel which slidably engages the tapered sides of the jaws. In this way, the actuator shaft may be advanced distally so as to engage sides of the jaws in the axial channel at the distal end of the actuator shaft. Upon engagement, the jaws will slide distally with the actuator shaft. Preferably, means are provided for limiting the distal movement of the jaws to a closing position adjacent the hook means. Upon reaching the closing position, further distal movement of the actuator shaft will slide the channel over the tapered sides of the jaws with the jaws remaining in a fixed axial position, thereby closing the jaws.

Various types of actuators may be provided to accomplish advancement and closure of the jaws. In one embodiment, a handle is secured to the proximal end of the shaft. The handle may be a variety of rigid biocompatible materials, such as stainless steel or a plastic such as acrylonitrile-butadiene styrene (ABS), Delrin ®, polycarbonate or the like. A lever is pivotally coupled to the handle, and a proximal end of the actuator shaft is coupled to the lever. In this way, pivoting the lever to a first position advances the jaws distally to a position adjacent the hook means, and further pivoting the lever from the first position to a second position closes the jaws so as to apply a clip to the tissue structure.

The apparatus will further include means for advancing clips through the axial passage of the shaft to the distal end and into the jaws. The clip feeding means may comprise any of a variety of mechanisms, such as those described in U.S. Pat. No. 5,084,057, U.S. Pat. No. 5,163,945, or U.S. Pat. No. 5,192,288, the disclosures of which have been incorporated herein by reference. In one exemplary embodiment, the means for feeding clips will comprise an axially-aligned clip passage which receives a plurality of clips, each clip oriented with the legs pointing in a distal direction. The clips will be lined up within the clip passage with the legs of each clip engaging the preceding clip. A spring-biased follower mechanism is provided in the clip passage behind the last clip so as to exert a constant distal force on the line of clips. A clip pusher is provided at the distal end of the clip passage, which, by actuating a lever on the handle, engages the distal-most clip in the clip passage and pushes the clip into the jaws through a guide passage.

Figures 1, 1A:
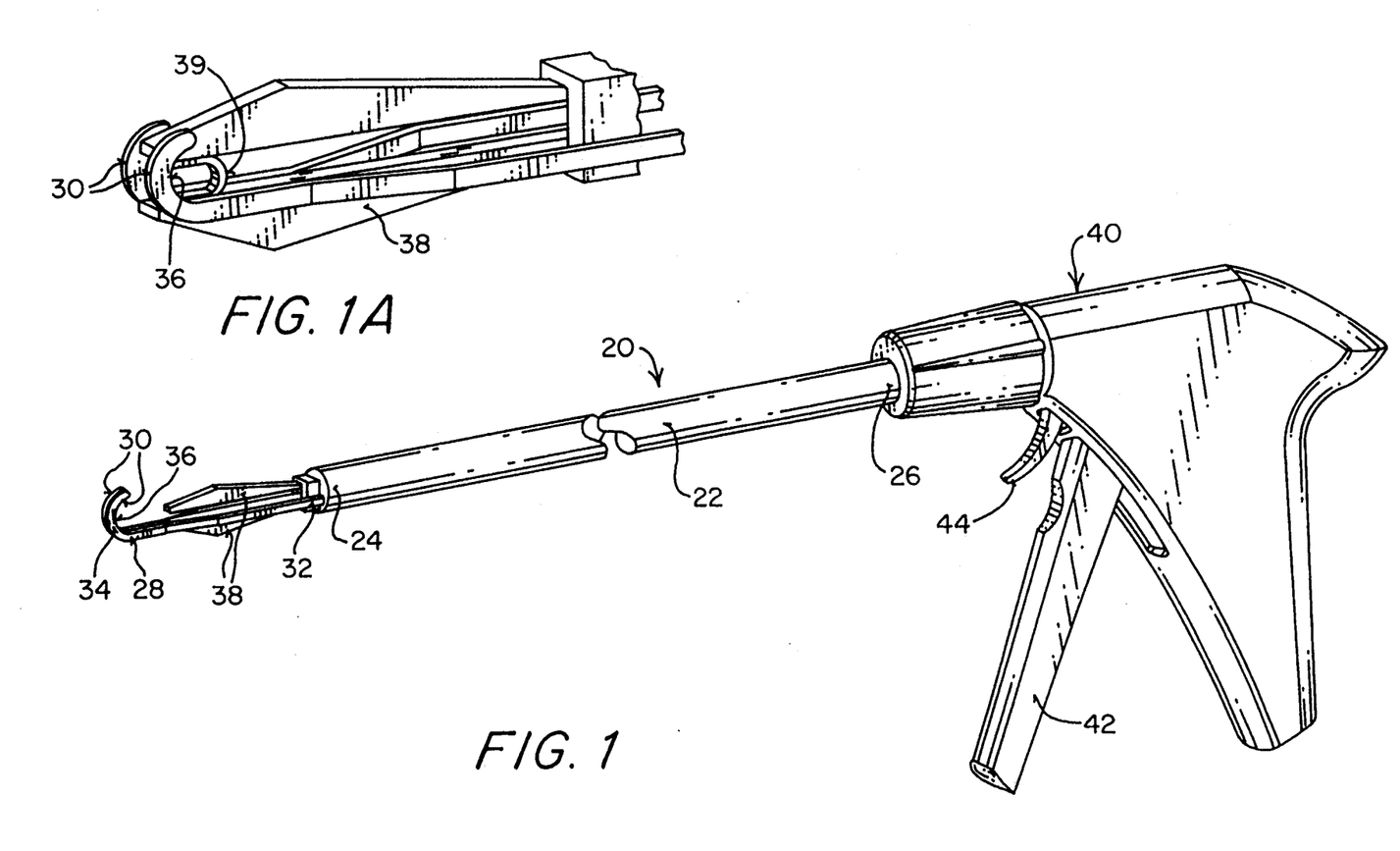
FIG. 1 is a perspective view of a surgical clip applier constructed in accordance with the principles of the present invention.
FIG. 1A is a perspective view of the distal end of the surgical clip applier of FIG. 1.

Referring now to FIG. 1, in a specific embodiment, clip applying apparatus 20 comprises an elongate rigid shaft 22 having a distal end 24 and proximal end 26. Hook means 28 is fixed to the distal end of shaft 22. Hook means 28 comprises a pair of hooks 30 having proximal ends 32 fixed to the shaft and distal ends 34. Hooks 30 have a distal portion defining a surface 36 facing in the proximal direction against which a tissue structure may be positioned and tensioned by drawing the shaft in the proximal direction. In a preferred embodiment, distal ends 34 of hooks 30 are laterally deflectable, and are biased inward toward one another for reasons which will become apparent below.

A pair of movable jaws 38 are slidably mounted to shaft 22 between hooks 30. Jaws 38 may be advanced distally to a position adjacent surface 36. In this way, a surgical clip positioned in jaws 38 may be advanced so that the legs of the clip surround a tissue structure retained in hooks 30, as described more fully below.

A handle 40 is secured to proximal end 26 of shaft 22 and is configured to be gripped by a single hand. A first lever 42 is pivotally mounted to handle 40 and serves to distally advance and close jaws 38 when pivoted toward handle 40. A second lever 44 pivotally mounted to handle 40 facilitates feeding surgical clips into jaws 38 after each clip application.

As illustrated in FIG. 1A, jaws 38 are disposed between hooks 30 with the side surfaces of the jaws sliding in contact with the inner lateral surfaces of the hooks. As the jaws move distally, hooks 30 spread apart so that, in the distal-most position, the hooks lie immediately adjacent jaws 38 with clip 39 held in the jaws adjacent proximally-facing surface 36. In this way, the distally-pointing legs of clip 39 will be disposed on opposing sides of a tissue structure positioned in hooks 30, positioning the clip for closure on the tissue structure.

Figures 2A, 2B, 2C:
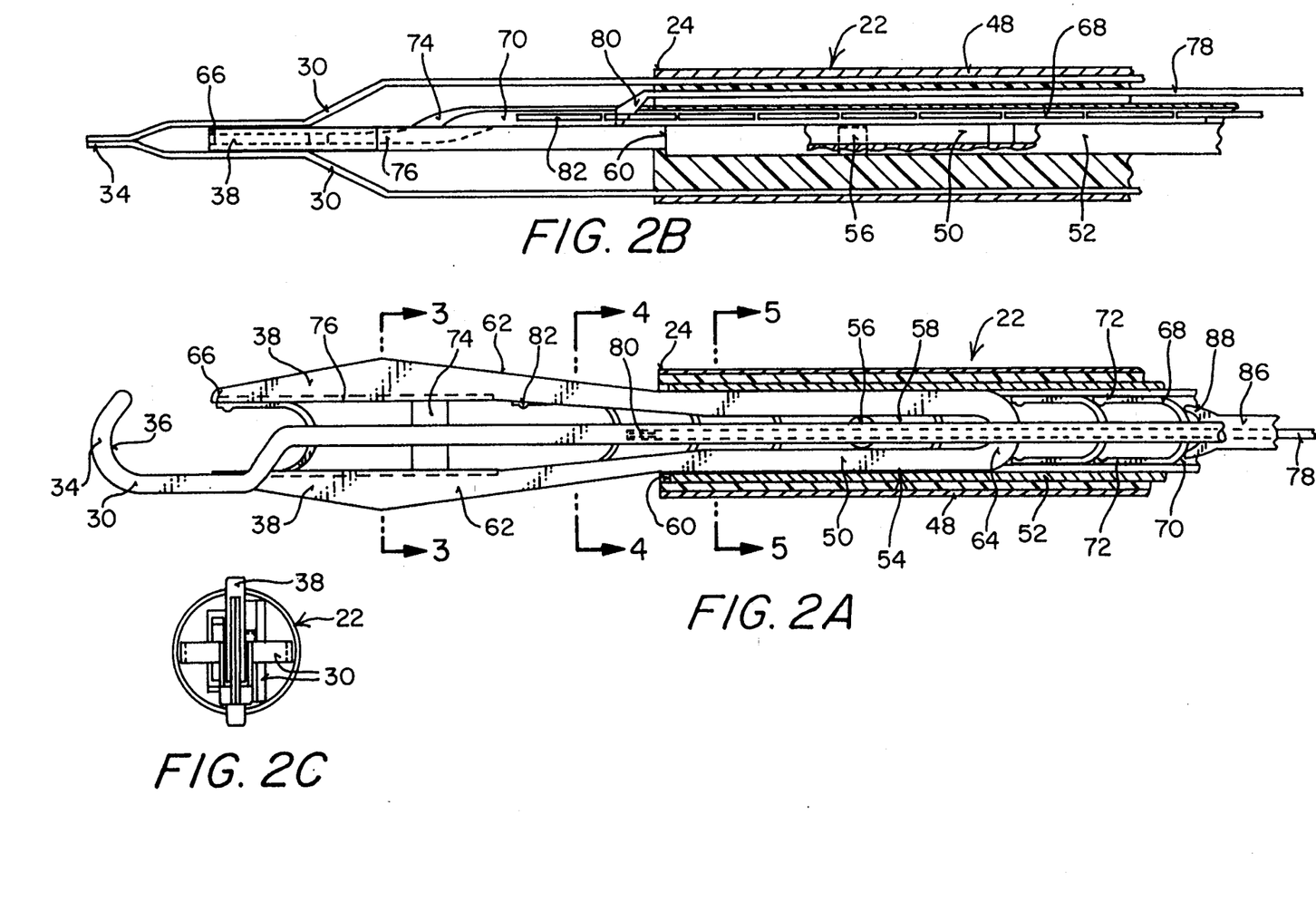
FIGS. 2A and 2B are side and top partial cutaway views of a distal portion of the clip applier of FIG. 1.
FIG. 2C is a distal end view of the clip applier of FIG. 1.
Figures 3, 5:
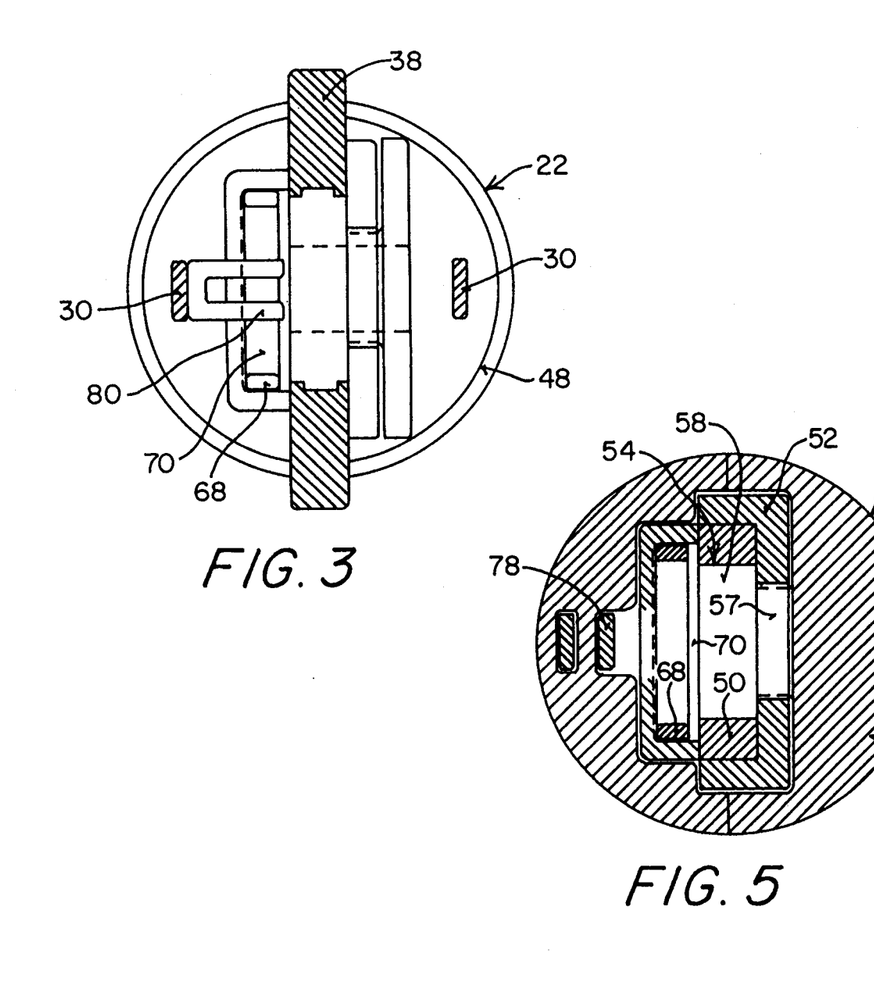
FIGS. 3, 4 and 5 are transverse cross-sectional views through lines 3—3, 4—4 and 5—5, respectively, in the distal portion of the clip applier of FIG. 2A.
Figure 4:
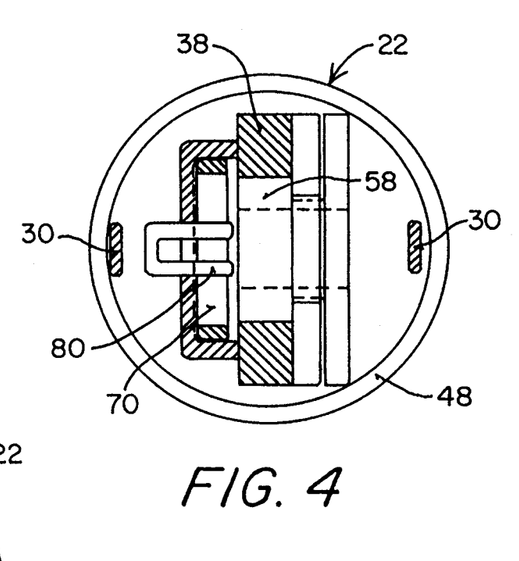

Referring now to FIGS. 2A-2C and FIGS. 3-5, shaft 22 comprises an outer tube 48, which may comprise two longitudinally divided tube halves. Jaws 38 have a proximal shank portion 50 disposed in the interior of tube 48. An actuator shaft 52 is slidably disposed in tube 48 and has an axial channel 54 which slides over shank portion 50 of jaws 38. As best seen in FIG. 5, a transverse pin 56 is secured to tube 48 and extends through an axial slot 57 in actuator shaft 52 and through an axial slot 58 in shank 50 of jaws 38. As shown in FIGS. 2A-2B, actuator shaft 52 has a distal end 60 configured to engage the tapered sides 62 of jaws 38 in axial channel 54. In this way, actuator shaft 52 may slide distally relative to jaws 38 until distal end 60 contacts the proximal end of tapered portion 62. This causes jaws 38 to move distally in tandem with actuator shaft 52 until the proximal end 64 of shank 50 engages pin 56. This limits further distal movement of jaws 38 relative to hook 30, and preferably leaves jaw 38 disposed in a position wherein the distal ends 66 of the jaws are adjacent the distal portions 34 of hooks 30, as shown in FIG. 1A. As actuator shaft 52 moves further distally, distal end 60 slides over tapered sides 62 of the jaws, thereby closing the jaws.

Clips 68 are fed serially from the proximal end of shaft 22 through a clip channel 70. Legs 72 of each clip point in the distal direction, with the distal ends of the legs contacting the preceding clip. At its distal end 74, clip channel 70 is angled toward jaws 38 so as to feed clips 68 into tracks 76 (shown in phantom) in jaws 38. A push rod 78 is slidably disposed in tube 48 and has a distal pusher 80 extending into clip channel 70. Pusher 80 will be laterally deflectable when engaged by clips 68 as they are fed distally so that the clips may pass to the distal side of pusher 80. As best shown in FIG. 3, pusher 80 has a bifurcated distal end so as to provide a balanced pushing force on the curved apex of each clip. Push rod 78 may be selectively advanced distally, as described below, so that pusher 80 advances the distal-most clip 82 in clip channel 70 into track 76 in jaws 38.

Clips 68 are urged distally by a slidable follower 86 disposed in clip channel 70 proximal to the proximalmost clip. Preferably, the distal end 88 of follower 86 will have a bifurcated configuration so as to provide a balanced distal force on the rounded proximal side of clips 68. Follower 86 will be urged in a distal direction by a tension spring (not shown) secured to tube 48, usually in a distal portion thereof.

It will be understood that the clip feeding mechanism of the invention is not limited to the embodiment illustrated in FIGS. 1-5, but may have any of a variety of configurations to which the distal hooks and jaws of the invention may be adapted. Other types of clip feed mechanisms suitable for use in the clip applier of the present invention are described, for example, in U.S. Pat. No. 5,192,288, U.S. Pat. No. 5,084,057 or U.S. Pat. No. 5,163,945, the complete disclosures of which have been incorporated herein by reference.

Figures 6A, 6B:
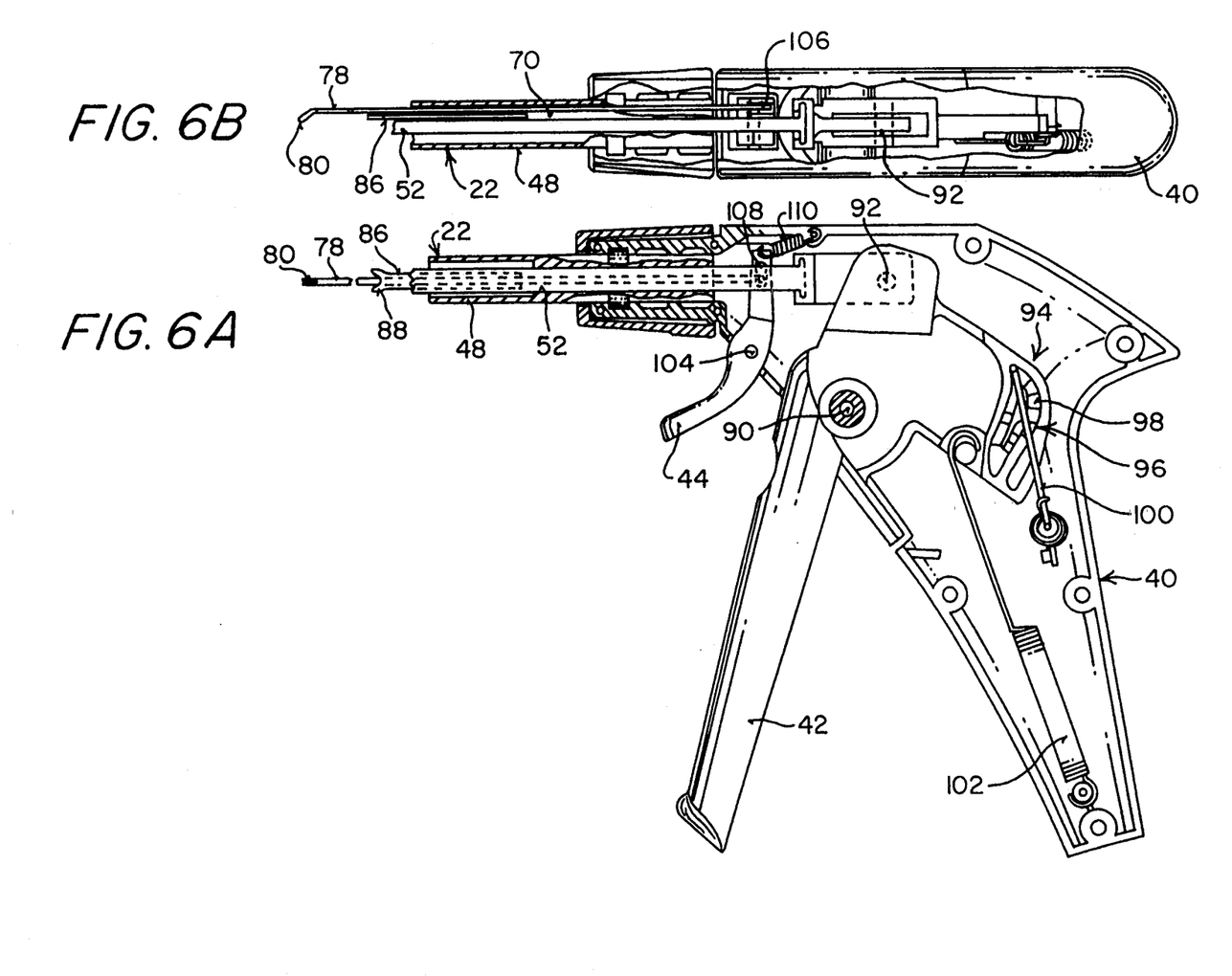
FIGS. 6A and 6B are side and top partial cutaway views of the handle and actuator of the surgical clip applier of FIG. 1.
Figure 7A:
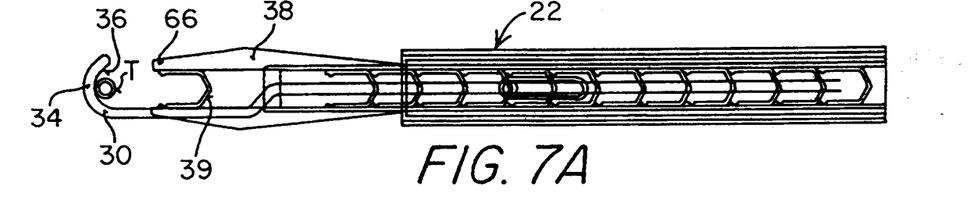
FIGS. 7-10 are side and top cross-sectional views of a distal portion of the clip applier of FIG. 1, illustrating a method performed in accordance with the principles of the present invention.
Figure 7B:
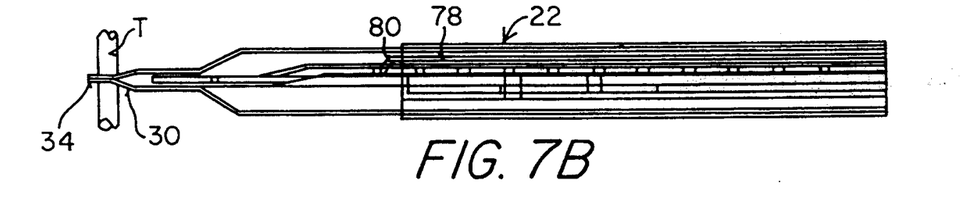

Referring now to FIGS. 6A and 6B, an exemplary embodiment of handle 40 of the clip applier of the invention will be described. Lever 42 is pivotally coupled to handle 40 by means of a pin 90. The proximal end of actuator shaft 52 is coupled to lever 42 by a pin 92. In this way, pivoting lever 42 toward handle 40 translates actuator shaft 52 distally through shaft 22. A ratchet mechanism 94 may be coupled to lever 42 to provide ratcheted actuation of the actuator shaft. In an exemplary embodiment, ratchet mechanism 94 comprises a track 96 having a plurality of steps 98, with a pall 100 configured to slide through track 96 as the lever 42 pivots. A spring 102 connected between handle 40 and lever 42 biases the lever in an outward position. Such a ratchet mechanism is described more fully in U.S. Pat. No. 5,192,288, the disclosure of which has been incorporated herein by reference.

A second lever 44 is pivotally mounted to handle 40 by means of a pin 104. At the upper end of lever 44, the proximal end 106 of push rod 78 is pivotally coupled to lever 44 in a slot 108. In this way, pivoting lever 44 toward handle 40 translates push rod 78 distally. A spring 110 secured to lever 44 and housing 40 biases the lever in an outward position.

Follower 88, urged by a tension spring (not shown) distally within clip channel 70, exerts a continual distal force on the line of clips in the clip channel. When a clip is to be applied, lever 44 is pivoted toward handle 40, translating push rod 78 in a distal direction, whereby pusher 80 at the distal end pushes the distal-most clip in the clip channel into jaws 38. Lever 44 is then released, retracting push rod 78. Lever 42 is then pivoted toward handle 40, which, in a first portion of its motion, translates actuator shaft 52 until its distal end contacts the tapered sides of jaws 38. The jaws are then translated distally with actuator shaft 52 to a position adjacent the distal portion 34 of hooks 30 (FIG. 2). As lever 42 is pivoted further toward handle 40, jaws 38 remain stationary relative to hooks 30 while actuator shaft 52 continues its distal movement relative to the jaws and the hooks. The engagement of the tapered sides of the jaws within the longitudinal channel of actuator shaft 52 urges the jaws toward one another, thereby closing the clip. Advantageously, ratchet mechanism 94 permits the user to release pressure on lever 42 at any point, and lever 42 along with actuator shaft 52 will remain in position. When the lever has been pivoted fully toward handle 40 so as to close the clip, releasing the lever will permit it to return to the outward position shown in FIG. 6A.

FIGS. 7-10 illustrate a preferred embodiment of the method of the present invention. Referring to FIG. 7A and 7B, a tissue structure T is engaged in hooks 30 with the tissue structure against proximally facing surface 36 in distal portion 34 of the hooks. At this point, jaws 38 are in a retracted position with a gap between the distal end 66 of the jaws and the distal portion 34 of the hooks. A clip 39 is illustrated as having been positioned in jaws 38 by means of push rod 78, in the manner described above. Advantageously, tissue structure T may be retained in hooks 30 and repositioned in the body cavity for improved access or visualization by manipulating shaft 22. Particularly advantageous is the ability to exert tension on tissue structure T so as to retract the tissue structure from adjacent tissue, eliminating the risk of clipping nearby organs or other tissue, as well as providing enhanced visualization.

Figure 8A:
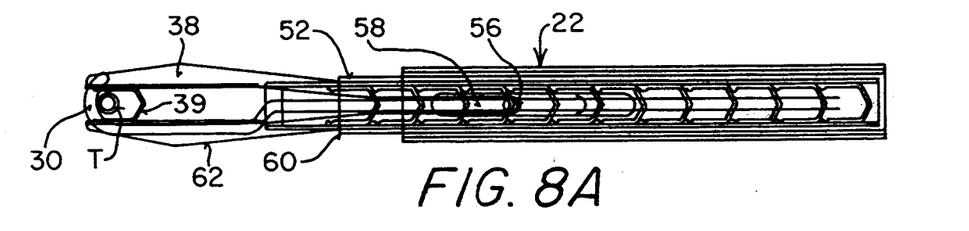
Figure 8B:
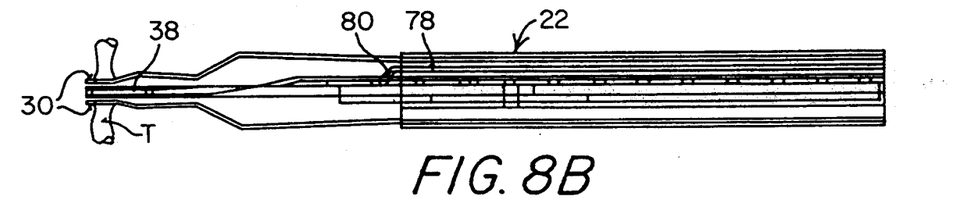

Referring to FIGS. 8A and 8B, jaws 38 are then advanced distally by translating actuator shaft 52 in a distal direction using lever 42 on handle 40 (described above). The distal end 60 of actuator shaft 52 engages the tapered sides 62 of jaws 38, initially translating jaws 38 distally in tandem with actuator shaft 52. As jaws 38 move distally, the side faces of the jaws engage the inner surfaces of hooks 30, urging the hooks apart. Jaws 38 will move distally until transverse pin 56 engages the proximal end of slot 58 in the shank portion of the jaws. In the position shown in FIGS. 8A and 8B, tissue structure T is supported on opposing sides of jaws 38 by each of hooks 30. Clip 39 is disposed with the legs of the clip on either side of tissue structure T.

Figure 9A:
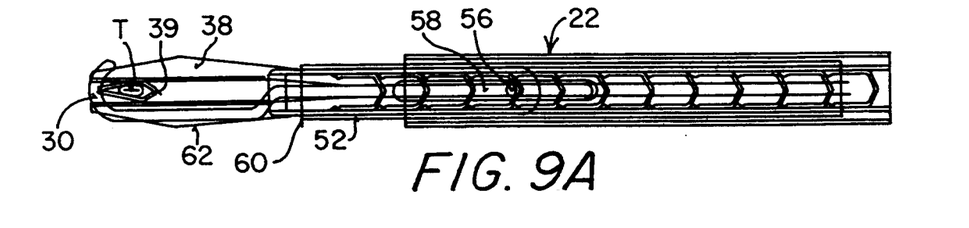
Figure 9B:
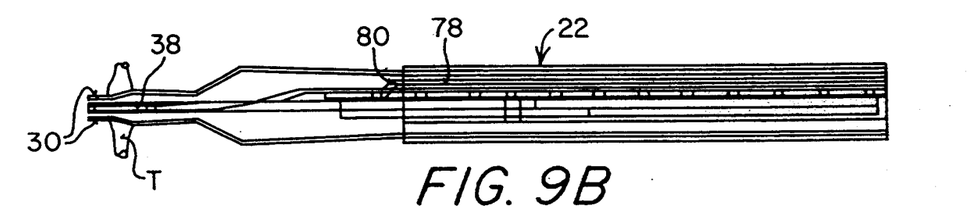
Figure 10A:
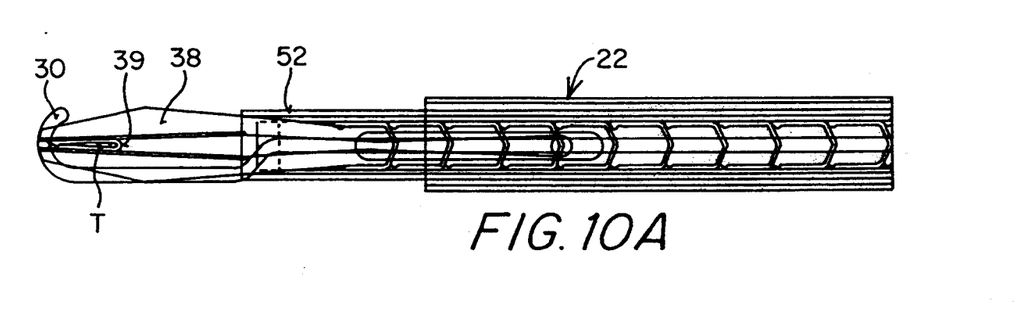
Figure 10B:
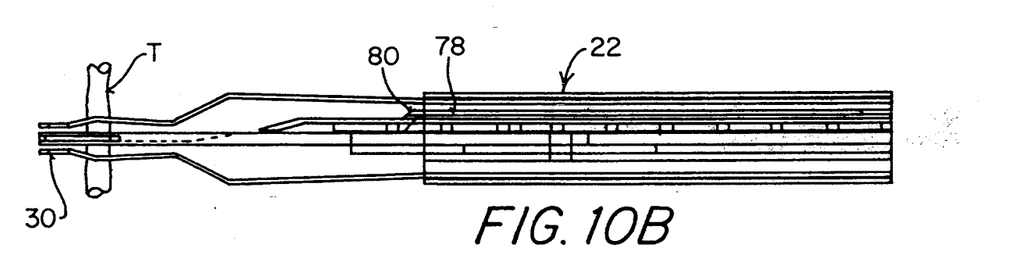

As shown in FIGS. 9A and 9B, further distal movement of actuator shaft 52 urges jaws 38 toward one another by the engagement of distal end 60 and channel 54 with tapered side surfaces 62 of the jaws. During jaw closure, jaws 38 remain in a stationary position relative to hooks 30. Clip 39 is thus closed On tissue structure T, to the configuration shown in FIGS. 10A and 10B. Once ligation is complete, lever 42 on handle 40 is released, retracting actuator shaft 52 and jaws 38 into shaft 22. The next clip may then be loaded into the jaws by actuating lever 44, whereby push rod 78 translates the distal-most clip into the jaws. Another tissue structure may then be positioned in hooks 30, and the process repeated.

Although the foregoing invention has been described in some detail by way of illustration and example for purposes of clarity of understanding, it will be obvious that certain changes and modifications may be practiced within the scope of the appended claims.

What is claimed is:

1. Apparatus for applying surgical clips to a tissue structure, the apparatus comprising:
    a shaft having a distal end and a proximal end, the shaft defining an axial direction;
    means, operably coupled to the shaft, for advancing a clip along the shaft to the distal end;
    hook means fixed to the distal end of the shaft, the hook means having a distal portion disposed transverse to the shaft so as to define a surface facing in a proximal direction for engaging a tissue structure;
    a pair of movable jaws at the distal end of the shaft axially slidable relative to the shaft for closing a clip on a tissue structure engaged by the hook means;
    means, operably coupled to the jaws, for advancing the jaws to a position adjacent the distal portion of the hook means; and
    means, operably coupled to the jaws for closing the jaws.

2. The apparatus of claim 1 wherein the hook means comprises a pair of hooks extending distally from the distal end of the shaft generally parallel to the axial direction, the jaws being disposed between the hooks.

3. The apparatus of claim 2 wherein the hooks have a proximal end fixed to the shaft and a distal end which is laterally deflectable, the distal ends being biased inward such that inner side faces of the hooks contact opposing lateral sides of the jaws as the jaws are moved distally.

4. The apparatus of claim 3 wherein the inner side faces of the hooks contact one another when the jaws are in a proximal position.

5. The apparatus of claim 1 wherein the shaft has an axial passage from the proximal end to the distal end, the means for advancing the jaws comprising an actuator shaft slidably disposed in the axial passage, the actuator shaft having a distal end for engaging the jaws to advance the jaws distally.

6. The apparatus of claim 5 wherein the jaws are fixed to a bifurcated member having a shank portion and a pair of prongs with tapered sides extending distally from the shank, the jaws being fixed to a distal end of the prongs, the actuator shaft having an axial channel configured to slidably engage the tapered sides so as to close the jaws as the actuator shaft is advanced distally relative to the jaws.

7. The apparatus of claim 6 wherein the tapered sides of the bifurcated member are biased outwardly so that the distal end of the actuator shaft engages the tapered sides of the bifurcated member to advance the jaws distally with the actuator shaft.

8. The apparatus of claim 1 wherein the shaft, jaws and hook means are configured to be introduced through a 10 mm cannula.

9. The apparatus of claim 1 wherein a plurality of clips are retained in the shaft.

10. Apparatus for applying surgical clips to a tissue structure, the apparatus comprising:
    a shaft having a distal end and a proximal end and an axial passage therebetween;.
    means, operably coupled to the shaft, for advancing a clip along the shaft to the distal end;
    hook means fixed to the distal end of the shaft, the hook means having a distal portion disposed transverse to the shaft so as to define a surface facing in a proximal direction for engaging a tissue structure;
    a pair of movable jaws at the distal end of the shaft axially slidable relative to the hook means for closing a clip on a tissue structure engaged by the hook means;
    means, operably coupled to the jaws, for advancing the jaws to a position adjacent the distal portion of the hook means, the advancing means comprising an actuator shaft slidably disposed in the axial passage, the actuator shaft having a distal end for engaging the jaws to advance the jaws distally;
    means, operably coupled to the jaws, for closing the jaws;
    the jaws being fixed to a bifurcated member having a shank portion and a pair of prongs with tapered sides extending distally from the shank, the jaws being fixed to a distal end of the prongs, the actuator shaft having an axial channel configured to slidably engage the tapered sides so as to close the jaws as the actuator shaft is advanced distally relative to the jaws; and
    means in the shaft for limiting distal movement of the jaws to a closing position adjacent the distal portion of the hook means, wherein the jaws remain open while being advanced to the closing position, and the jaws are closed while remaining at the closing position.

11. Apparatus for applying surgical clips to a tissue structure, the apparatus comprising:
    a shaft having a distal end and a proximal end and an axial passage therebetween;
    means, operably coupled to the shaft, for advancing a clip along the shaft to the distal end;
    hook means fixed to the distal end of the shaft, the hook means having a distal portion disposed transverse to the shaft so as to define a surface facing in a proximal direction for engaging a tissue structure;
    a pair of movable jaws at the distal end of the shaft axially slidable relative to the hook means for closing a clip on a tissue structure engaged by the hook means;
    means, operably coupled to the jaws, for advancing the jaws to a position adjacent the distal portion of the hook means, the advancing means comprising an actuator shaft slidably disposed in the axial passage, the actuator shaft having a distal end for engaging the jaws to advance the jaws distally;

means, operably coupled to the jaws, for closing the jaws;

the jaws being fixed to a bifurcated member having a shank portion and a pair of prongs with tapered sides extending distally from the shank, the jaws being fixed to a distal end of the prongs, the actuator shaft having an axial channel configured to slidably engage the tapered sides so as to close the jaws as the actuator shaft is advanced distally relative to the jaws; and a handle secured to the proximal end of the shaft and a lever pivotally coupled to the handle, the lever being further coupled to a proximal end of the actuator shaft, wherein pivoting the lever to a first position advances the jaws distally, and pivoting the lever from the first position to a second position closes the jaws.

12. An improved surgical clip applier of the type having an elongate shaft with a distal end, a proximal end and an axial passage therebetween, a pair of U-shaped movable jaws pointing in the distal direction at the distal end of the shaft, means for advancing a surgical clip into the jaws, and means for closing the jaws, the improvement comprising:

hook means fixed to the distal end of the shaft for holding a tissue structure in tension as the surgical clip is closed, wherein the jaws are axially slidable relative to the shaft.

13. The surgical clip applier of claim 12 wherein the hook means comprises a pair of hooks extending from the distal end of the shaft generally parallel to the axial direction, the jaws being disposed between the hooks.

14. The surgical clip applier of claim 12 further comprising means for advancing the jaws distally to a position adjacent the hook means, the means for advancing comprising an actuator shaft slidably disposed in the axial passage having a distal end for engaging the jaws to advance the jaws distally.

15. The surgical clip applier of claim 14 wherein the jaws have tapered sides, the actuator shaft having an axial channel for slidably engaging the tapered sides of the jaws to close the jaws as the actuator shaft is advanced distally relative to the jaws.

16. An improved surgical clip applier of the type having an elongate shaft with a distal end, a proximal end and an axial passage therebetween, a pair of U-shaped movable jaws pointing in the distal direction at the distal end of the shaft, means for advancing a surgical clip into the jaws, and means for closing the jaws, the improvement comprising:

hook means fixed to the distal end of the shaft for holding a tissue structure in tension as the surgical clip is closed, wherein the jaws are axially slidable relative to the hook means;

means for advancing the jaws distally to a position adjacent the hook means, the means for advancing comprising an actuator shaft slidably disposed in the axial passage having a distal end for engaging the jaws to advance the jaws distally;

the jaws having tapered sides, the actuator shaft having an axial channel for slidably engaging the tapered sides of the jaws to close the jaws as the actuator shaft is advanced distally relative to the jaws; and a handle secured to the proximal end of the shaft and a lever pivotally coupled to the handle, the lever being further coupled to a proximal end of the actuator shaft, wherein pivoting the lever to a first position advances the jaws and pivoting the lever from the first position to a second position closes the jaws.

17. A method of applying surgical clips to a tissue structure, the method comprising:

engaging the tissue structure in a hook fixed to a distal end of a shaft of a clip applier;

exerting a proximally-directed force on the shaft so as to hold the tissue structure in tension;

advancing a U-shaped clip into a pair of movable jaws at the distal end of the shaft;

distally advancing the jaws relative to the shaft such that the tissue structure is disposed between the jaws; and closing the clip on the tissue structure with legs of the clip pointing distally while holding the tissue structure in tension.

18. The method of claim 17 wherein the step of advancing a clip is performed before the step of distally advancing the jaws.

19. The method of claim 17 wherein the step of distally advancing the jaws comprises actuating an actuator coupled to a handle secured to a proximal end of the shaft.

20. The method of claim 19 wherein actuating the actuator further closes both jaws on the tissue structure.

21. A method of applying surgical clips to a tissue structure, the method comprising:

engaging the tissue structure in a hook fixed to a distal end of a shaft of a clip applier;

exerting a proximally-directed force on the shaft so as to hold the tissue structure in tension, the proximally-directed force being exerted using a handle fixed to a proximal end of the shaft, the hook being in a fixed position relative to the handle;

advancing a U-shaped clip into a pair of movable jaws at the distal end of the shaft;

distally advancing the jaws relative to the hook such that the tissue structure is disposed between the jaws; and closing the clip on the tissue structure with legs of the clip pointing distally while holding the tissue structure in tension.

22. The method of claim 21 wherein the step of advancing a clip is performed after the step of distally advancing the jaws.

23. The method of claim 21 further comprising inserting a distal portion of the shaft through a percutaneous cannula into a body cavity, the tissue structure being disposed within the body cavity.

24. The method of claim 23 wherein the percutaneous cannula has an interior diameter of at most about 10 mm.

* * * * *